United States Patent [19]

Forssmann et al.

[11] Patent Number: 4,809,682

[45] Date of Patent: Mar. 7, 1989

[54] UNDERWATER ELECTRODES FOR CONTACTLESS LITHOTRIPSY

[75] Inventors: Bernd Forssmann, Friedrichshafen; Harald Eizenhoefer, Johannesberg, both of Fed. Rep. of Germany

[73] Assignee: Dornier Medizintechnik GmbH, Munich, Fed. Rep. of Germany

[21] Appl. No.: 940,023

[22] Filed: Dec. 10, 1986

[30] Foreign Application Priority Data

Dec. 12, 1985 [DE] Fed. Rep. of Germany ....... 3543881

[51] Int. Cl.⁴ ............................................ A61B 17/22

[52] U.S. Cl. .................................. 128/24 A; 128/328

[58] Field of Search .............. 128/24 A, 328; 367/147

[56] References Cited

U.S. PATENT DOCUMENTS

| | | | |
|---|---|---|---|
| 2,559,227 | 7/1951 | Rieber | 128/24 A |
| 3,286,226 | 11/1966 | Kearsley et al. | 367/147 |
| 3,347,336 | 10/1967 | Nash | 367/147 |
| 3,416,128 | 12/1968 | Allen | 367/147 |
| 3,785,382 | 1/1974 | Schmidt-Kloiber et al. | 128/328 |

FOREIGN PATENT DOCUMENTS

| | | | |
|---|---|---|---|
| 2635635 | 2/1978 | Fed. Rep. of Germany | 128/328 |

*Primary Examiner*—Ruth S. Smith

*Attorney, Agent, or Firm*—Ralf H. Siegemund

[57] ABSTRACT

An underwater electrodes assembly for contactless lithotripsy is suggested wherein two electrodes have tips facing each other across a narrow gap and at least one, preferably both, electrodes are surrounded by sleeves or rings made of a dielectric material, such as a thermoplastic.

8 Claims, 1 Drawing Sheet

UNDERWATER ELECTRODES FOR CONTACTLESS LITHOTRIPSY

BACKGROUND OF THE INVENTION

The present invention relates to an underwater electrode assembly for contactless lithotripsy whereby particularly the tips of two electrodes face each other in close proximity to each other but with a clear and definite separation for establishing a spark gap.

At the present time it is a successful practice of long standing to comminute concrements in the body of human beings and in a manner which does not require invasive surgery and therefore does not require physical engagement with the concrement. Instead, acoustical shock waves are used which break up the concrement into sufficiently small pieces so that by natural discharge process these pieces (grit, dust) will be removed from the body. Shock waves for this purpose are produced by means of underwater spark discharges and the gap is arranged in the focal point of a water filled focusing chamber having a wall constructed to follow a rotational ellipsoid. As the spark jumps across the gap between the electrodes, a shock wave is produced. The energy is derived from the discharge of an electric capacitor.

Electrodes of the type that is suitable for such shock wave generation are known through German patent 26 35 635. Particularly FIG. 4 of that patent shows electrodes which are very satisfactory in practice. Generally speaking these electrodes include a tubular outer conductor which is continued in a yoke or cagelike configuration having an apex on which is mounted an electrode pointing inwardly into the cage. An inner conductor which traverses the first mentioned tubular outer conductor, but is electrically insulated therefrom, just ends in an electrode tip which faces the tip of the first mentioned electrode.

The generally coaxial configuration of the electrodes as described establishes a steady transition of the electrical field lines as they emerge from the inner conductor towards the outer conductor but also towards the cage and primarily to the tip of the first mentioned elecrode. The spark in the gap should, as much as possible, be produced directly along and in the electrode axis because that axis traverses precisely the focal point of the rotational ellipsoid. Initially this operation is quite certain. However, after so many uses the tips of the electrodes, no matter how refractory they are, will in fact begin to burn off which changes their contour in a basically unforseeable manner consequently the exact disposition of the arc whenever it occurs may randomly vary. This means that the arc may at times extend slightly off the focal points.

In addition certain misfirings will occur; initially only very rarely but as time progresses these misfirings may occur to an increasing extent which means that several plasma channels are established during a single discharge. The shock wave generation will become less and less concentrated and becomes somewhat fuzzy and only more or less in the vicinity of the focal point. In fact these misfirings can be acoustically ascertained; they are recognizable in contradistinction to the usual sharp sound as more muted beats. Needless to say that as soon as these various defects occur the electrodes have to be exchanged. An off-focus generation of the spark gap means that the refocusing of the shock waves as they have been reflected by the rotational ellipsoid, will not occur with a sufficiently high density and possible even off the second focus. That second focus is in the concrement to be comminuted. A slight off center ear may not be that dangerous if the concrement is of sufficient size but a reduction in shock wave density simply reduces the effectiveness of such shock wave. The breaking process is in fact impeded.

DESCRIPTION OF THE INVENTION

It is an object of the present invention to increase the use life of underwater electrodes for contactfree lithotripsy of the type mentioned above.

It is a specific object of the present invention to improve underwater electrodes which have tips arranged to face each other for precise positioning in a focal point.

It is suggested in accordance with the preferred embodiment to provide, near the tip of at least one of the electrodes, a sleeve or diaphragm made of a dielectric material. In other words the invention introduces a second dielectric material; the first one being the water in which the electrodes are submerged. This second dielectric is contoured as a sleeve or a diaphragm and that will increase the use life of these electrodes. In fact tests have indicated that the use life will increase threefold.

The invention makes use of the fact that electrical field lines are refracted at the interface between two dielectric materials with different dielectric coefficients. Water has a dielectric coefficient of about 80 which as compared with many solid dielectric materials is very high so that a high dielectric polarization obtains. If now a sufficiently convenient and suitably diametrically contoured dielectric material is added with a coefficient in the order of 2 to 3 then in fact the field line distribution between the electrodes is controlled in a very convenient fashion. The arc is more or less forced to occur in the axis of the electrodes even if certain statistically unforeseeable burn off effects occur right at the tip proper, the arc will still to a considerably lesser degree scatter as to its contour around the focal point. A variety of configurations for the dielectric material were found to be suitable. The front face for example should be planar, or convexly, or concavely curved. Preferably, the front face of the dielectric sleeve on one of the electrodes is convex and the front face of the sleeve on the other electrode is concave.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Figure 1:
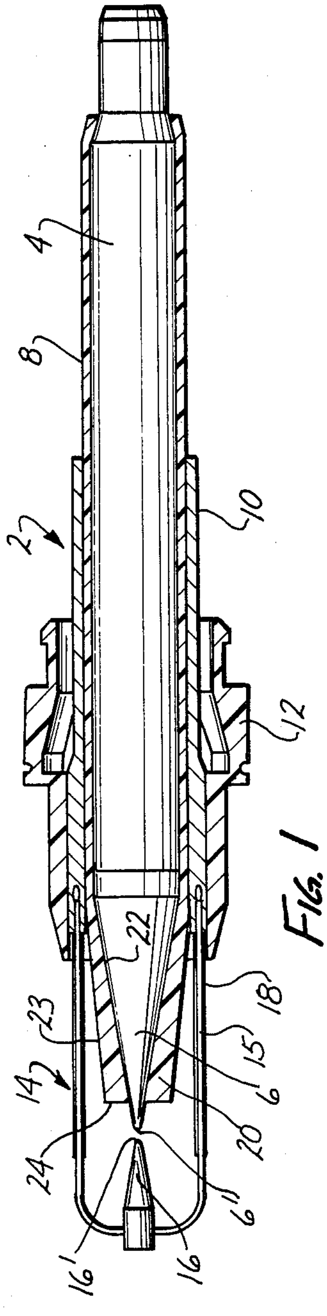
FIG. 1 is a cross section through an electrode assembly in accordance with the preferred embodiment of the present invention for practicing the best mode thereof showing a dielectric sleeve on one of the electrodes.

Proceeding now to the detailed description of the drawings FIG. 1 serves as illustration for the first embodiment of the present invention and illustrating an electrode assembly 2 in its entirety. The electrode assembly 2 includes an inner conductor 4 which ends in an electrode 6 having a tip 6'. The conductor is surrounded by electrical insulation 8. In addition there is provided an outer conductor 10 combined with and held by a mounting sleeve 12. By means of sleeve 12 one will fasten the electrode assembly 2 in a holder which is not shown and by means of that holder the electrode is fastened to a reflector body having its interior shaped as a rotational ellipsoid. The conductors 10 and 4 are connected to an electrical circuit which is not shown. That connection occurs upon insertion of the electrodes in the aforementioned housing. Examples for mounting and refinements concerning mounting particulars, details and accuracy are disclosed by way of example in application Ser. No. 917,854, filed Oct. 14, 1986 of common assignee.

The outer conductor 10 is continued in a cagelike configuration 14 being comprised of several wire loops 15 which, so to speak, extend forward from the conductor 10 loop around (90 degrees) and at their end the wires carry a second electrode 16 having a tip 16', being, so to speak, inwardly directed, into the cage as defined by the wires 15. The wires 15 are covered in parts by electrically insulated sleeves 18.

The two tips 6' and 16' face each other at a narrow gap. The inner conductor 4 as well as the outer conductor 10 as continued in the cage are made of metallic material. The electrodes 6 and 16 are made of metal but with additional requirements and here tungsten, tantalum, or other fireproof materials and alloys are preferred. The electrical insulation 8 as well as the mounting sleeve 12 are made of synthetic material.

A sleeve 20 has been shrunken upon the electrode 6. The sleeve 20 is made of a material of high impact ductility and suitable dielectric constant. It was found that a particular thermoplastic material traded by Bayer, Leverkusen, under the trade name Pocan is very suitable. This material has a dielectric constant of 3.0 for 20 degrees C. and at a frequency of 1 megaH. In addition it is of advantage to have a material used for that purpose which is acoustically similar to water as much as possible and it should particularly be permeable that is to way produce as little reflection of shock waves as possible, because any reflection of of shock waves at the material introduces stray and scattered radiation which, in turn, reduces the effectiveness of the shock wave generation. In particular diffraction and dispersion of shock waves produced should be avoided. The sleeve 20 has a conical bore 22 and a jacket 23 that is also conical. In this particular embodiment the sleeve 20 is provided with a planar front face 20 i.e. which is the face directed towards the gap. Moreover it may be of advantage to use a single piece as illustrated that is to say the sleeve 20 and the insulation 8 is a single piece element and made of the same material.

Figure 2:
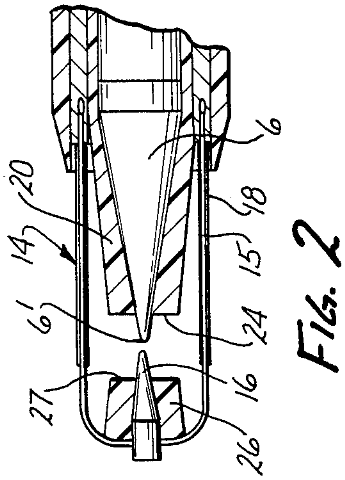

FIG. 2 shows an electrode construction which, as a whole, is the same as in FIG. 1; there is however that difference, namely in FIG. 1 no sleeve is provided on electrode 16 while a sleeve 26 is placed onto electrode 16 as per FIG. 2. This sleeve 26 is likewise made of the same material as the sleeve 20. The geometry of the sleeve 26 matches that of electrode 6 and the front face 28 is likewise planar.

Figure 3:
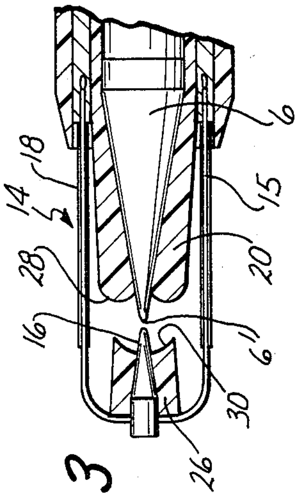
FIGS. 2, 3 and 4 are views similar to FIG. 1 with emphasis on the electrode tip area showing differently contoured dielectric sleeves or rings on one or both electrodes.

Generally speaking the geometry of the sleeves, the wall thickness in addition to the chosen material and the contour of the end faces are in effect parameters which are available for optimizing the concentration and distribution of the electric field lines. As shown in FIG. 3 the particular elements are in fact similar to the elements shown in FIG. 2 except that the sleeve 20' has a concave front face 28 and the sleeve 26' has a concave front face 30. The relation could be reversed. It was found that the concave convex complementary kind of face structure of these facing sleeves provides for a better confinement and stability of the electric field line.

Figure 4:
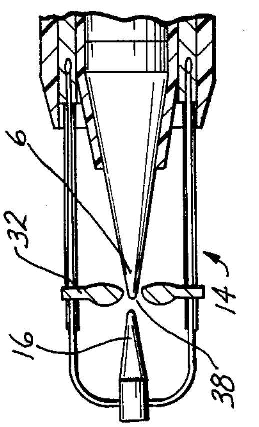

FIG. 4 illustrates an alternative example for practicing the invention. Here a dielectric ring 32 is provided with a bore 34 and is fastened on the cage 14. The cross section of the ring is somewhat torroidal so that in fact in acoustical lens type aperture obtains. Other geometries are possible and can be practiced.

The invention is not limited to the embodiments described above but all changes and modifications thereof not constituting departures from the spirit and scope of the invention are intended to be included.

We claim:

1. Underwater electrode assembly for contactless lithotripsy wherein the assembly includes first and second electrodes ending in tips facing each other to define a narrow gap the improvement comprising:

at least one of said electrodes having a conical portion that converges towards the tip of the electrode, that conical portion being surrounded by a dielectric sleeve or ring, being in contact with surrounding water.

2. The assembly as in claim 1 the sleeve having a front face, the front face of the sleeve being planar.

3. Electrode assembly as in claim 1 wherein dielectric sleeves or rings are mounted on both electrodes.

4. The electrode assembly as in claim 3 wherein at least one of the sleeves has a convex front face.

5. The electrode assembly as in claim 3 wherein at least one of the sleeves has a concave front face.

6. Electrode assembly as in claim 3 wherein one of said sleeves has a concave front face the other one having a convex front face.

7. Electrode assembly as in claim 1 wherein one of the electrodes is mounted on a cage, the ring of dielectric material being connected to said cage.

8. An electrode assembly for contactless lithotripsy including first and second electrodes of tapering configuration ending in tips, said tips facing each other across a narrow gap, said electrodes provided for immersion and contact with water, the improvement of at least one ring or sleeve of conical configuration enveloping a part of the tapering portion of one of the electrodes and being made of a dielectric material, the dielectric constant being significantly different from the dielectric constant of water.

* * * * *